(12) United States Patent  
Kaup

(10) Patent No.: US 8,317,788 B2
(45) Date of Patent: Nov. 27, 2012

(54) INTRAMEDULLARY PIN FOR INSERTION INTO THE MEDULLARY SPACE OF A FEMUR

(75) Inventor: Thomas Kaup, Davos Frauenkirch (CH)

(73) Assignee: Synthes USA, LLC, West Chester, PA (US)

( * ) Notice: Subject to any disclaimer, the term of this patent is extended or adjusted under 35 U.S.C. 154(b) by 818 days.

(21) Appl. No.: 11/787,261

(22) Filed: Apr. 13, 2007

(65) Prior Publication Data

US 2007/0288017 A1 Dec. 13, 2007

Related U.S. Application Data

(63) Continuation of application No. PCT/IB2004/003425, filed on Oct. 20, 2004.

(60) Provisional application No. 60/522,568, filed on Oct. 14, 2004.

(51) Int. Cl.
*A61B 17/72* (2006.01)

(52) U.S. Cl. ............... 606/62; 606/64; 606/67

(58) Field of Classification Search ............ 606/62–68
See application file for complete search history.

(56) References Cited

U.S. PATENT DOCUMENTS

| | | | | | |
|---|---|---|---|---|---|
| 4,103,683 | A | * | 8/1978 | Neufeld | 606/67 |
| 4,135,507 | A | * | 1/1979 | Harris | 606/62 |
| 4,630,601 | A | * | 12/1986 | Harder et al. | 606/62 |
| 5,472,444 | A | * | 12/1995 | Huebner et al. | 606/64 |
| 5,562,667 | A | * | 10/1996 | Shuler et al. | 606/64 |
| 5,779,705 | A | * | 7/1998 | Matthews | 606/67 |
| 5,879,352 | A | * | 3/1999 | Filoso et al. | 606/62 |
| 6,106,528 | A | * | 8/2000 | Durham et al. | 606/64 |
| 6,120,504 | A | * | 9/2000 | Brumback et al. | 606/62 |
| 6,210,414 | B1 | * | 4/2001 | Lin | 606/64 |
| 6,461,360 | B1 | * | 10/2002 | Adam | 606/67 |
| 6,547,791 | B1 | * | 4/2003 | Buhren et al. | 606/62 |
| 6,579,294 | B2 | * | 6/2003 | Robioneck | 606/64 |
| 7,247,156 | B2 | * | 7/2007 | Ekholm et al. | 606/64 |
| 2002/0183750 | A1 | * | 12/2002 | Buhler | 606/62 |
| 2003/0069581 | A1 | * | 4/2003 | Stinson et al. | 606/62 |

* cited by examiner

*Primary Examiner* — Alvin Stewart
*Assistant Examiner* — Jerry Cumberledge
(74) *Attorney, Agent, or Firm* — Fay Kaplun & Marcin, LLP

(57) ABSTRACT

An intramedullary pin for insertion into the medullary space of the femur through the lateral compacta of the trochanter major. The pin has a proximal pin section and an adjoining distal pin section. Each pin section includes one or more bores for one or more bone screws. The proximal pin section has at least one bore running obliquely to the longitudinal axis, so that bone screws can be inserted through the bore into the head of the femur, or a screw can be inserted in the antegrade direction through the bore. The distal pin section is at least partly straight and the proximal pin section has a curvature in the lateral-posterior direction.

15 Claims, 3 Drawing Sheets

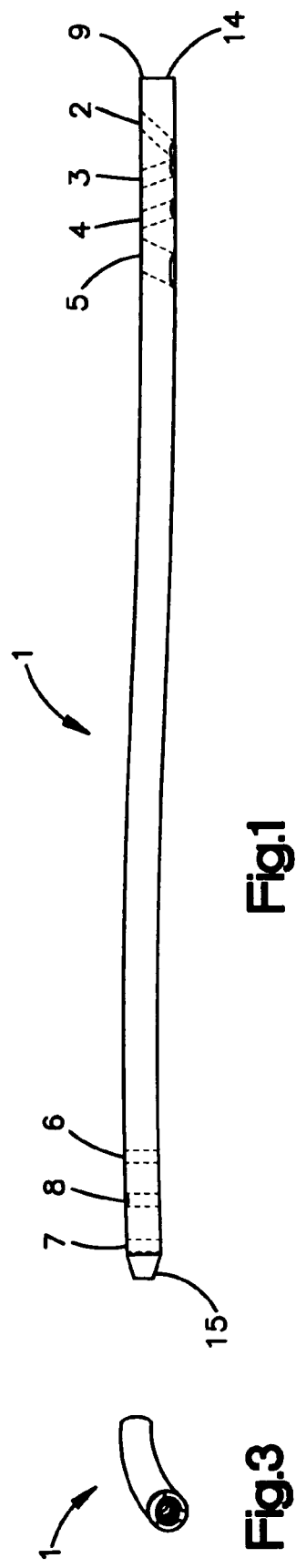
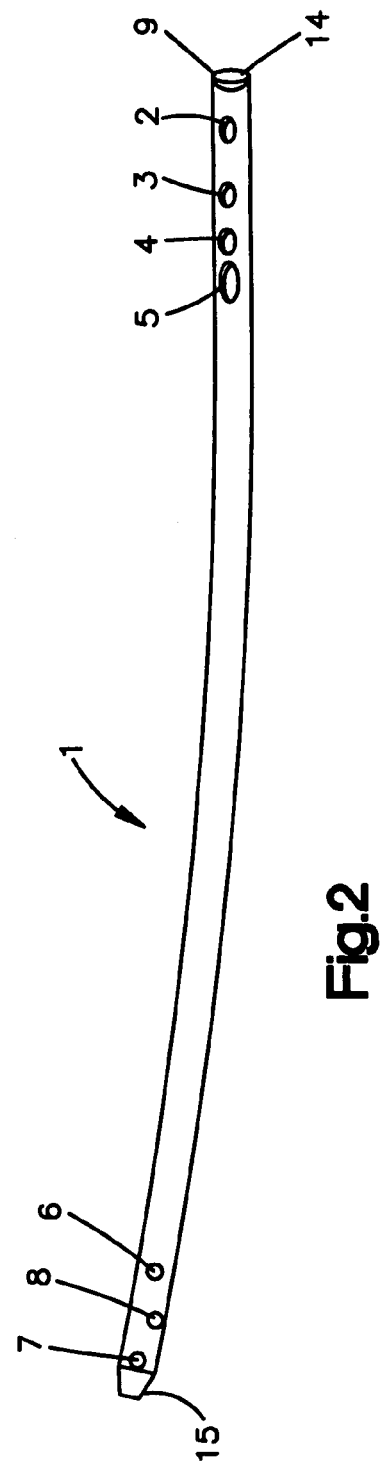
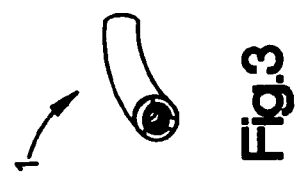

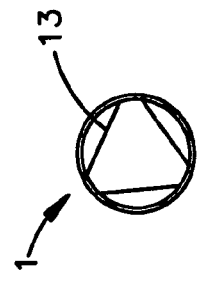
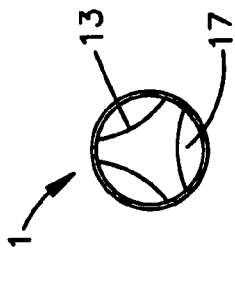
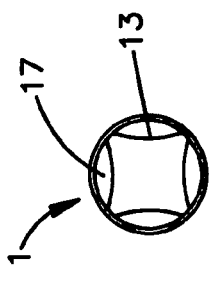
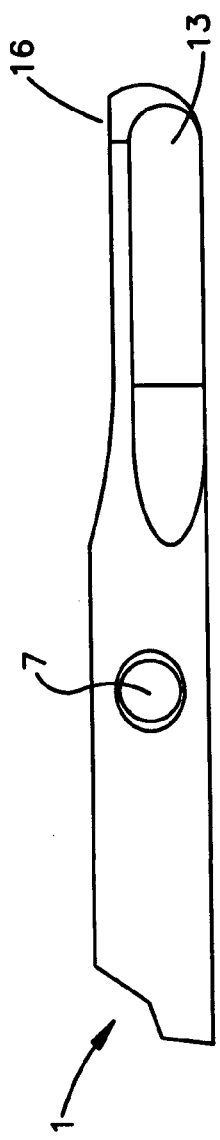
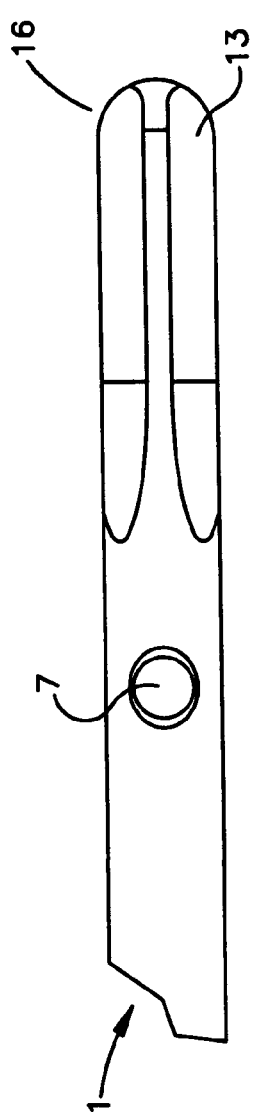
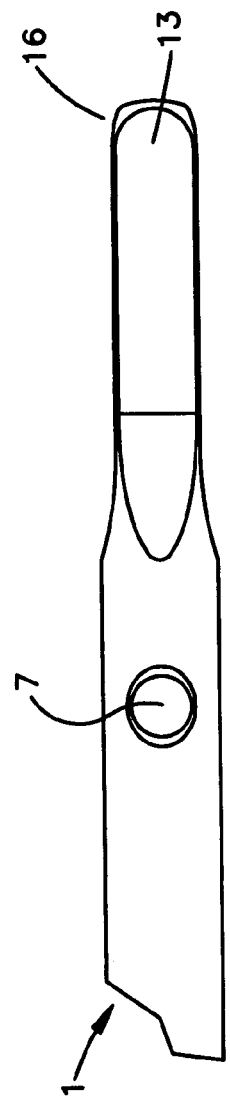

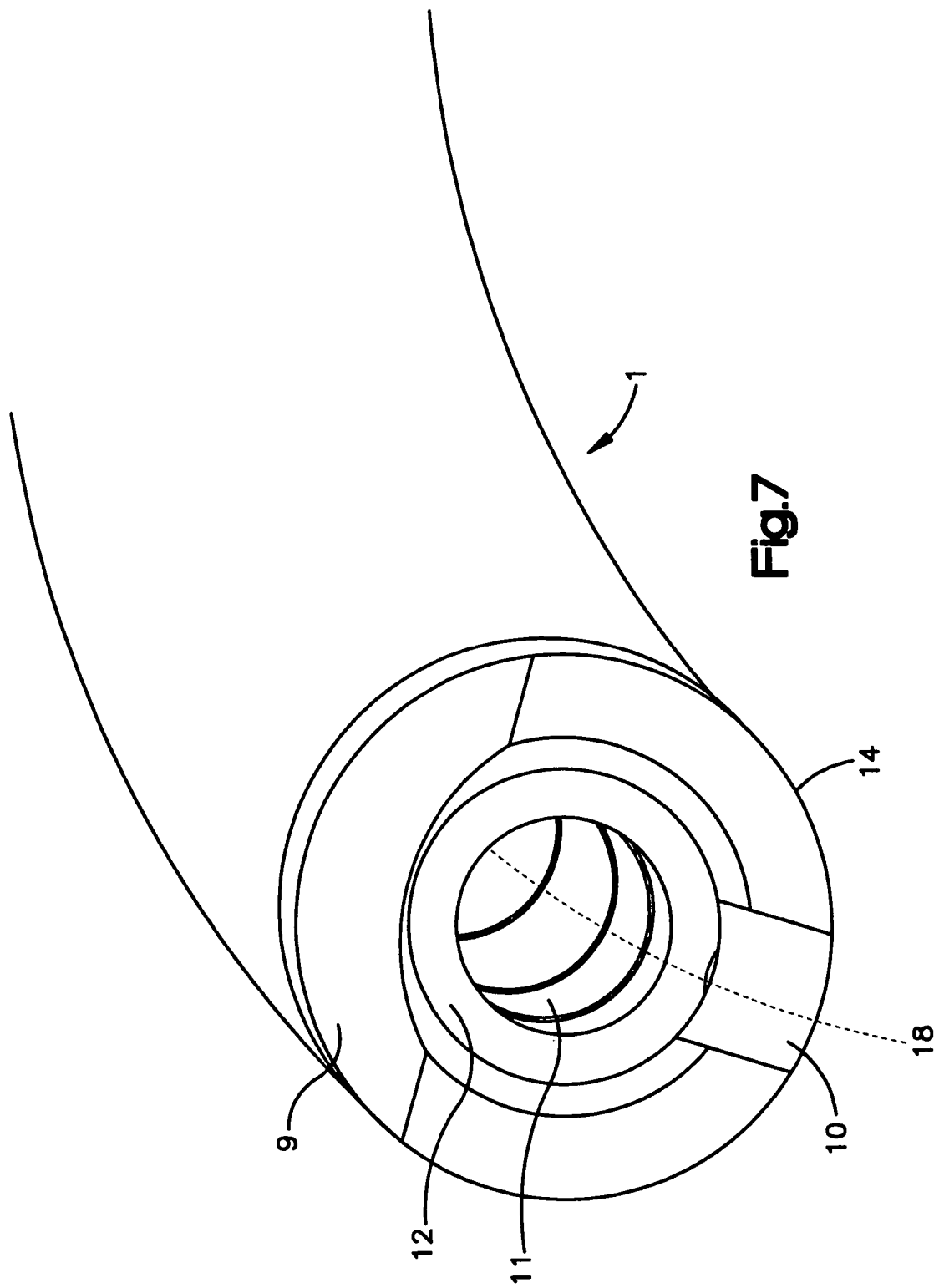

INTRAMEDULLARY PIN FOR INSERTION INTO THE MEDULLARY SPACE OF A FEMUR

CROSS REFERENCE TO RELATED APPLICATION

This application is a continuation of International Patent Application No. PCT/IB2004/003425, filed Oct. 20, 2004, the entire contents of which is expressly incorporated herein by reference.

TECHNICAL FIELD

The present invention relates an intramedullary pin for insertion into the medullary space of a femur.

BACKGROUND OF THE INVENTION

It is known in the art to use intramedullary pins. U.S. Pat. No. 6,461,360B1 describes an intramedullary pin for osteosynthesis. Before insertion into a femur, the intramedullary pin has, at its distal end, in the sagittal plane, a curvature which corresponds to the counter-curvature of the femur. The proximal end substantially has a continuous curve with constant radius of curvature in the frontal plane.

U.S. Pat. No. 6,010,506 discloses a hybrid pin having different radii, all of which extend in a plane.

International publication WO 02089683 discloses an intramedullary pin using helix geometry. This structure ensures that the entry point for a pin inserted in an antegrade direction can be displaced laterally from the trochanter tip. On insertion of the pin, the pin rotates through about 90°. The rotation of the pin is influenced substantially by its helix geometry. The inner wall of the medullary space and spongiosa serve here as a guide structure.

There are disadvantages to using a pure helical geometry in varying anatomy of bones. In one instance, on reaching the end position, the distal locking holes may not be in lateral medial alignment. To correct this, the pin must be either inserted further or drawn back. The pin would rotate about its longitudinal axis as a result of either being inserted further or being drawn back. This consequently results in an undesired change of height of the locking position. On reaching the end position, the screws thus cannot be introduced centrally through the neck of the femur for locking in the head of the femur. In another instance, if only rotation is to be corrected, this can lead to a displacement of the implant depth of the pin and hence to an undesired change in the height of the locking position. If the proximal pin end is not yet completely in the bone, the pin must be inserted more deeply. This, however, results in an undesired continuation of the rotational movement. As a result of this, the optimum positions of the locking options are once again changed.

SUMMARY OF THE INVENTION

The present invention is to provide a remedy for the above-discussed disadvantages. It is an object of the invention to create an intramedullary pin where the distal locking holes are preferably parallel to the frontal plane or in lateral/medial alignment when the pin comes to rest in its final implantation depth range. The intramedullary pin may then be fixed in the proximal region by means of screws which are inserted through the neck of the femur into the head of the femur. To accomplish this, the implantation depth of the pin must be such that the screws may be passed centrally through the neck of the femur. The neck of the femur and head are, however, rotated relative to the frontal plane about the longitudinal axis of the femur. This rotation is described as the anteversion angle, meaning that the pin must be adapted to the anatomically changing anteversion angles by rotation of the pin about its longitudinal axis. This is intended to ensure that the screws may be placed centrally through the neck of the femur and centrally in the head. Furthermore, the proximal pin end should be flush with the surrounding cortex or deeper. This is intended to prevent the surrounding tissue from being irritated by the proximal pin end.

It is therefore an object to provide an intramedullary pin that need not have an adapted geometry for every femur bone exhibiting different growth, in order to fulfill the abovementioned conditions. The present invention accomplishes the objective set out above with an intramedullary pin where the end of the helical shape are modified. Specifically, the proximal end of the pin is curved in a plane, while the distal end remains straight. This ensures that, on reaching the final implantation depth range, the intramedullary pin ceases to rotate by itself. In the final implantation depth range, the pin may be displaced along its longitudinal axis without change of rotation. The pin may nevertheless be arbitrarily rotated about its longitudinal axis without changing its implantation depth.

While the distal pin section therefore has, at least partly, no curvature at all, the proximal pin section run traverses the lateral posterior direction when it is inserted into the medullary space through the lateral compacta of a trochanter major.

By changing the ends of the helical shape, it is possible to produce an intramedullary pin which functions optimally for a certain group of bones. Variation in anatomy no longer has an effect on the functionality of the pin. The intramedullary pin may be optimally oriented for locking in the bone.

The intramedullary pin according to the invention preferably has, in the proximal region, at least has two bores running obliquely to the longitudinal axis and parallel to one another and a third bore intersecting the first two bores. The orientation of the three bores allows for a combination of possibilities for locking the intramedullary pin, where antegrade locking has particular importance. A new lateral opening for the intramedullary pin approximately coincides with the insertion direction of the antegrade screw. If only one screw is set proximally, no further skin incision is therefore necessary.

In another embodiment, the pin preferably has two bores running transverse to the pin's longitudinal axis and parallel to one another and, at the distal end, a bore which is arranged in between the two bores, is rotated about the longitudinal axis relative to the plane defined by the two bores and likewise runs transverse to the pin's longitudinal axis. The middle locking bore is rotated through 25° relative to the left and right locking bores. A feature of the distal arrangement of the three bores lies in the combination of the possibilities for locking. In addition to the generally known standard locking, a third bore is present between the two standard bores. By locking the pin with three screws, axial stability is achieved. This ensures that the position of the distal pin end is fixed and the pin cannot be displaced on the screws. The 25° angle of the axial blocking screw may prevent the screw from injuring important soft tissues during insertion. This can occur, for example, if the screw is inserted in the sagittal direction (90°). The locking screws may be present at a distance of about 30 mm away from one another.

In another embodiment, an intramedullary pin, having a longitudinal/pin axis, for insertion into a medullary space of a femur through the lateral compacta of the trochanter major, comprises a proximal pin section and an adjoining distal pin section, respectively having a proximal end plane and distal end plane. The proximal pin section includes a proximal end, a 120° antegrade bore compatible with a locking screw having a thickness of about 5.0 mm thick, and a cranial 130° recon bore compatible with a headless screw of about 6.5 mm thick, where the recon bore coincides medially with the antegrade bore. The proximal pin section also includes a caudal 130° recon bore compatible with a headless screw having a thickness between about 3.9-6.0 mm, and an oval bore for static and dynamic positioning of a locking screw having a thickness of about 3.9-6.0 mm. The distal pin section includes a tip, two bores transverse to the longitudinal axis of the pin and parallel to one another; and an anterolateral bore rotated through 25° relative to the two bores.

For proper implantation, it is very important to be able to recognize the end of the pin clearly with the aid of an imaging method (X-rays). This is not possible or possible only to an insufficient extent according to the prior art to date. Incorrect insertion depth might have the following consequences: if the pin does not come to rest sufficiently deep in the bone, the projecting pin end may result in complications such as pain, necrosis, etc. If the pin is implanted too deep, the result may be offset of the proximal pin end. Furthermore, ingrowth of bone may occur so that the upper part of the original insertion channel is closed. These possibilities complicate the subsequent explanation of the intramedullary pin (implant). Moreover, there is the danger that the tip of the pin will penetrate into the knee.

For introduction of the implant, the pin is connected to a target bow. This usually rests flat on the end of the pin. It results in a continuous transition and contour matching between pin and target bow. A bevel which interrupts the transition and the contour matching between the target bow and pin is preferably formed laterally at the proximal end of the pin according to the invention. In the case of an anterior-posterior X-ray photograph, the end of the pin is, as a result, easily and clearly detectable. This simplifies the surgery and leads to safer use and a shorter operation time. The pin entry point is on the lateral surface of the trochanter major. This surface can be palpated particularly in slim patients. This means that the surface is covered only by a thin layer of skin. Through the lateral entry point of the pin, it is necessary to prevent the soft tissue from being irritated by the proximal pin end. An advantage of the bevel is that the bevel also ensures that the proximal pin end fits the lateral cortex wall with a matching contour. This prevents irritation of the soft tissue.

A groove by means of which the rotation of the pin on the target bow is fixed is preferably present on the medial side of the proximal end. In comparison, the prior art comprises rotational fixing via two grooves, which, however, result in a higher manufacturing cost.

A cylindrical recess into which the diametrically opposite shaft of the connecting screw can penetrate between the target bow and pin is present at the proximal end. Consequently, the pin axis is aligned coaxially with the target bow, the thread exerting only the contact pressure. In comparison, the prior art comprises the coaxial alignment directly and only by the thread of the connecting screw.

A special formation of the tip allows the pin to be tapped without rotation into the spongiosa in the distal femur region. This prevents rotation of the pin even without the use of a locking screw. The tip of the pin has, in a radial section, differing from the circular shape, special tip surfaces, in particular concave notches or planar surfaces. Use of such tips prevent subsequent, arbitrary or involuntary rotation is not possible.

BRIEF DESCRIPTION OF THE DRAWINGS

The intramedullary pin is explained in even greater detail in the following exemplary drawings. The intramedullary pin may be better understood by reference to the following drawings, wherein like references numerals represent like elements. The drawings are merely exemplary to illustrate the structure, operation and method of use of the intramedullary pin and certain features that may be used singularly or in combination with other features and the invention should not be limited to the embodiments shown.

The invention is explained in more detail schematically and by way of example with reference to figures.

FIG. 1 shows an intramedullary pin according to one embodiment of the invention viewed in the anterior to posterior direction, i.e. in the lateral-medial plane, FIG. 2 shows the intramedullary pin viewed in the lateral to medial direction, i.e., in the anterior-posterior plane, FIG. 3 shows the intramedullary pin viewed in the proximal to distal direction, FIG. 4a shows a particular embodiment of the tip of the pin viewed in the lateral to medial direction, FIG. 4b shows a particular embodiment of the tip of the pin viewed in the distal to proximal direction, FIG. 5a shows a particular embodiment of the tip of the pin viewed in the lateral to medial direction, FIG. 5b shows a particular embodiment of the tip of the pin viewed in the distal to proximal direction, FIG. 6a shows a particular embodiment of the tip of the pin viewed in the lateral to medial direction, FIG. 6b shows a particular embodiment of the tip of the pin viewed in the distal to proximal direction and FIG. 7 shows the proximal end of the tip viewed in the proximal to distal direction.

DESCRIPTION OF THE PREFERRED EMBODIMENTS

FIGS. 1-3 depict an intramedullary pin 1 in three views. The intramedullary pin 1 has a proximal end 14 and a distal end 15. The shaft of the pin 1 is generally cylindrical in shape. The proximal end 14 may be curved in a lateral-posterior direction, while the distal end 15 may be straight or at least partly straight. Proximal and distal end planes of the pin may be rotated about 60°-110°, preferably 70°-90° and in particular 80° relative to one another. In one embodiment, the radius is between about 300-1300 mm, preferably about 900-1200 mm and in particular about 1100 mm. The length of the proximal radius corresponds to the lateral contact surface with the cortex which is about 300-1000 mm, preferably about 600-800 mm, and in particular 700 mm.

The length of the distal straight section may correspond to the depth to which the distal pin end penetrates into the distal spongiosa structure. The length may be about 35-70 mm, preferably about 40-60 mm, and in particular about 52 mm.

The pin 1, at the proximal end 14, may be designed with a 120° antegrade bore 2 compatible with a locking screw having a thickness between about 3.9-6.0 mm, a cranial 130° recon bore 3 compatible with a headless screw that is about 6.5 mm thick. The 130° recon bore 3 may coincide medially with the 120° antegrade bore 2. The pin 1 may further be designed with a caudal recon bore 4 which is approximately 130° and compatible with a headless screw that is about 6.5 mm thick, and an oval bore 5 for static and dynamic positioning of a locking screw that is about 3.9-6.0 mm thick. Furthermore, a lateral bevel 9 is recognizable at the proximal end 14. The orientation of the three bores 3, 4, 5 allows for a combination of possibilities for locking the intramedullary pin, where antegrade locking has particular importance. A lateral opening 2 for the intramedullary pin approximately coincides with the insertion direction of the antegrade screw. If only one screw is set proximally, no further skin incision is therefore necessary.

At the distal end 15, two bores 6 and 7 extend transverse to the pin's axis 18 and parallel to one another. An anterolateral bore 8 which is rotated through about 25° relative to the parallel bores 6 and 7 is shown at the distal end 15. The angle formed between the anterolateral bore 8 and the parallel bores is preferably between about 45° and 10°, where 0° corresponds to the frontal plane or the plane of two standard locking screws. A feature of the configuration of the three bores lies in the combination of the possibilities for locking. In addition to the generally known standard locking, the third bore 8 is present between the two standard bores. By locking the pin with three screws, axial stability is achieved. This ensures that the position of the distal pin end is fixed and the pin cannot be displaced on the screws. The 25° angle of the axial blocking screw may prevent the screw from injuring important soft tissues during insertion. This can occur, for example, if the screw is inserted in the sagittal direction (90°). The locking screws may be present at a distance of about 30 mm away from one another.

Special formations at the tip 16 of the pin 1 allows the pin 1 to be tapped without rotation into the spongiosa in the distal femur region so as to be secured, preventing rotation even without locking by means of a screw. The tip 16 of the pin 1 may have, in a radial section, differing from the circular shape (cylindrical) of the body of the pin 1, special tip surfaces, in particular concave notches or planar surfaces. In these embodiments, subsequent, arbitrary or involuntary rotation is not possible.

FIGS. 4a and 4b depict an embodiment of the tip 16 at the distal end 15 of the pin 1 in two views. The tip 16 may have, in a radial section, differing from the circular shape, special tip surfaces 13, in particular three planar surfaces, having a length of about 10-40 mm, preferably about 15-25 mm and in particular about 20 mm. The total length of the tip 16 may be about 20-50 mm, preferably about 25-35 mm and in particular 30 mm. Bore 7 is shown near the tip 16 of the distal end 15.

FIGS. 5a and 5b depict another embodiment of the tip 16 at the distal end 15 of the pin 1 in two views. The tip 16 may have, in a radial section, differing from the circular shape, special tip surfaces 13, in particular three concave notches, having a length of about 10-40 mm, preferably about 15-25 mm and in particular about 20 mm, and a radius 17 of about 4-10 mm, preferably about 5-8 mm and in particular about 6 mm. The total length of the tip 16 is about 20-50 mm, preferably about 25-35 mm and in particular about 30 mm.

FIGS. 6a and 6b depict another embodiment of the tip 16 at the distal end 15 of the pin 1 in two views. The tip 16 may have, in a radial section, differing from the circular shape, special tip surfaces 13, in particular four concave notches, which have a length of about 10-40 mm, preferably about 15-25 mm and in particular about 20 mm, and a radius 17 of about 4-10 mm, preferably about 5-8 mm and in particular about 6 mm. The total length of the tip 16 is about 20-50 mm, preferably about 25-35 mm and in particular about 30 mm.

FIG. 7 shows the proximal end 14 of the pin 1 viewed in a proximal to distal direction. A lateral bevel 9, discussed previously, may form an angle at the lateral-proximal end relative to the axial pin axis 18 of between about 10° to 60°, preferably about 40°. A cylindrical recess 12 may have a thread 11, and a positioning groove 10 on the medial side of the proximal end 14, are shown.

The bevel 9 which interrupts the transition and the contour matching between the target bow and pin 1 is preferably formed laterally at the proximal end 14 of the pin 1. In the case of an anterior-posterior X-ray photograph, the end of the pin 1 can be easily and clearly detectable. This simplifies the surgery and leads to safer use and a shorter operation time. The pin's entry point is on the lateral surface of the trochanter major. This lateral surface can be palpated particularly in slim patients. This means that the surface is covered only by a thin layer of skin. Through the lateral entry point of the pin 1, it is necessary to prevent the soft tissue from being irritated by the proximal end 14 of the pin 1. An advantage of the bevel 9 is that the bevel 9 may ensure that the proximal end 14 fits the lateral cortex wall with a matching contour. This may prevent irritation of the soft tissue.

While the distal pin section has, at least partly, no curvature at all, the proximal pin section may run in the lateral posterior direction when it is inserted into the medullary space through the lateral compacta of a trochanter major. The groove 10 which fixes the rotation of the pin 1 on the target bow is preferably present on the medial side of the proximal end 14. The cylindrical recess 12 into which the diametrically opposite shaft of a connecting screw can penetrate between target bow and pin 1 is present at the proximal end 14. Consequently, the pin axis 18 is aligned coaxially with the target bow, and the thread 11 exerts only contact pressure.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:
1. An intramedullary pin configured for insertion into a medullary space of a femur through the lateral compacta of the trochanter major, comprising:
a proximal pin section lying in a proximal end plane and an adjoining distal pin section lying in a distal end plane, the proximal pin section having a first proximal bore configured to receive at least one bone screw and a second proximal bore configured to receive at least one bone screw and the distal pin section having at least one distal bore configured to receive at least one bone screw,
wherein, a first bore axis of the first proximal bore extends obliquely to a longitudinal axis of the intramedullary pin, so that at least one bone screw can be inserted through the proximal bore into the head of the femur, and
wherein a second bore axis of the second proximal bore extends obliquely to a longitudinal axis of the intramedullary pin, wherein the first bore axis and the second bore axis coincide on a medial wall of the intramedullary pin;
wherein the distal pin section is at least partly straight and the proximal pin section has a curvature in the lateral- posterior direction, the distal pin section having at least three planar faces defining an outer profile thereof.

2. An intramedullary pin according to claim 1, wherein a bone screw can be inserted through an antegrade bore in the proximal pin section instead of through the first and second proximal bores.

3. An intramedullary pin according to claim 1, wherein the proximal and distal end planes are rotated about 60° to 110° relative to one another and the radius of the pin is about 300-1300 mm.

4. An intramedullary pin according to claim 3, wherein the length of the proximal pin section corresponds to a lateral contact surface with a cortex, and in that the proximal pin section has a radius of about 300-1000 mm.

5. An intramedullary pin according to claim 1, wherein the distal pin section has a length corresponding to a depth at which the distal pin end in an implanted state penetrates into distal spongiosa structure and is about 35-70 mm.

6. An intramedullary pin according to claim 5, wherein the pin is formed in such a way that, on reaching its final implantation depth range, the pin ceases to rotate by itself and, in the final implantation depth range, can be displaced along its longitudinal axis without changing rotation, and in that the pin can be rotated arbitrarily about its longitudinal axis in the final implantation depth range without changing its implantation depth.

7. An intramedullary pin, having a longitudinal/pin axis, for insertion into a medullary space of a femur through the lateral compacta of the trochanter major, comprising:
a proximal pin section lying in a proximal end plane and an adjoining distal pin section lying in a distal end plane, wherein the proximal pin section includes:
a proximal end;
a 120° antegrade bore compatible with a locking screw about 5.0 mm thick;
a cranial 130° recon bore compatible with a headless screw about 6.5 mm thick, wherein the recon bore coincides medially with the antegrade bore;
a caudal 130° recon bore compatible with a headless screw having a thickness of about 3.9-6.0 mm; and
an oval bore for static and dynamic positioning of a locking screw having a thickness of about 3.9-6.0 mm thick,
wherein an outer profile of the distal pin section is defined by at least three planar faces and includes:
a tip; and
two bores transverse to the longitudinal axis of the pin and parallel to one another; and,
an anterolateral bore rotated 25° relative to the two bores.

8. An intramedullary pin according to claim 7, wherein the proximal pin section has a lateral bevel having an angle of about 10° to 60° to the longitudinal axis at the lateral-proximal end.

9. An intramedullary pin according to claim 7, wherein a transition and contour matching between the proximal pin section and a target bow which can be caused to engage the intramedullary pin is interrupted.

10. An intramedullary pin according to claim 7, wherein the intramedullary pin has a single positioning groove at the proximal end.

11. An intramedullary pin according to claim 7, wherein the intramedullary pin has, at the proximal end, a cylindrical recess with a thread.

12. An intramedullary pin according to claim 11, wherein an intramedullary pin axis through the cylindrical recess is aligned coaxially with a target bow, and the thread exerts only contact pressure.

13. An intramedullary pin according to claim 7, wherein the tip is structured so that the intramedullary pin can be axially tapped into spongiosa in a distal femur region, the intramedullary pin being configured to prevent rotation without use of one or more locking screws.

14. An intramedullary pin according to claim 13, wherein the intramedullary pin has a length of approximately 20-50 mm, and wherein the three planar faces are concave notches having a length of about 10-40 mm and a radius of about 4-10 mM.

15. An intramedullary pin according to claim 13, wherein the intramedullary pin has a length of approximately 20-50 mm, and wherein the at least three planar surfaces have a length of about 10-40 mm.

* * * * *